United States Patent
Mahendra et al.

(10) Patent No.: US 12,361,557 B2
(45) Date of Patent: Jul. 15, 2025

(54) SYSTEMS AND METHODS FOR MONITORING ONE OR MORE ANATOMICAL ELEMENTS

(71) Applicant: Medtronic Navigation, Inc., Louisville, CO (US)

(72) Inventors: Nikhil Mahendra, Broomfield, CO (US); Shai Ronen, Westminster, CO (US); Victor D. Snyder, Erie, CO (US); Andrew J. Wald, Denver, CO (US); Steven Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 462 days.

(21) Appl. No.: 17/516,299

(22) Filed: Nov. 1, 2021

(65) Prior Publication Data

US 2022/0198665 A1    Jun. 23, 2022

Related U.S. Application Data

(60) Provisional application No. 63/128,574, filed on Dec. 21, 2020.

(51) Int. Cl.
*G16H 30/40* (2018.01)
*A61B 34/10* (2016.01)
(Continued)

(52) U.S. Cl.
CPC .......... *G06T 7/0014* (2013.01); *A61B 34/10* (2016.02); *G06T 7/20* (2013.01); *G16H 20/40* (2018.01);
(Continued)

(58) Field of Classification Search
CPC .................................................. G06T 7/0012
See application file for complete search history.

(56) References Cited

U.S. PATENT DOCUMENTS

| 10,555,779 B2 | 2/2020 | Kemp et al. |
| 2015/0243055 A1* | 8/2015 | Nishiyama .............. G06T 19/20 382/131 |

(Continued)

FOREIGN PATENT DOCUMENTS

| AU | 2017268489 | 5/2018 |
| CN | 101053012 | 10/2007 |

(Continued)

OTHER PUBLICATIONS

Grupp et al. "Pose Estimation of Periacetabular Osteotomy Fragments with Intraoperative X-Ray Navigation," arXiv.org, Mar. 22, 2019, 19 pages.

(Continued)

*Primary Examiner* — Di Xiao
(74) *Attorney, Agent, or Firm* — Sheridan Ross P.C.

(57) ABSTRACT

Systems and methods for monitoring one or more anatomical elements are provided. An image depicting one or more anatomical elements and a plurality of annotations may be received. The image may comprise a plurality of image elements. Each annotation may correspond to one of the one or more anatomical elements and may be associated with one of the plurality of image elements. Movement information about movement of at least a portion of a particular anatomical element may be received. Image elements corresponding to the particular anatomical element may be identified to yield a set of image elements. The set of image elements may be adjusted based on the movement information to yield an updated image reflecting changes to affected anatomical elements.

12 Claims, 4 Drawing Sheets

(51) Int. Cl.
  *G06T 7/00* (2017.01)
  *G06T 7/20* (2017.01)
  *G16H 20/40* (2018.01)

(52) U.S. Cl.
  CPC .... *G16H 30/40* (2018.01); *G06T 2207/10116* (2013.01); *G06T 2207/30012* (2013.01)

(56) References Cited

U.S. PATENT DOCUMENTS

| | | | |
|---|---|---|---|
| 2015/0302310 A1* | 10/2015 | Wernevi | G16H 50/20 706/12 |
| 2018/0185113 A1* | 7/2018 | Gregerson | A61B 34/30 |
| 2020/0090408 A1* | 3/2020 | Virkar | G06V 10/764 |
| 2020/0205898 A1 | 7/2020 | Hampp et al. | |
| 2020/0405395 A1* | 12/2020 | Gullotti | A61B 17/7082 |
| 2021/0081716 A1* | 3/2021 | Namioka | G06V 40/10 |
| 2021/0100526 A1* | 4/2021 | Schein | G06T 7/251 |
| 2022/0198669 A1* | 6/2022 | Chen | A61B 34/20 |
| 2022/0358773 A1* | 11/2022 | Thienphrapa | A61B 1/0005 |

FOREIGN PATENT DOCUMENTS

| | | | |
|---|---|---|---|
| CN | 101309358 | 11/2008 | |
| CN | 108720807 | 11/2018 | |
| CN | 108882854 | 11/2018 | |
| CN | 109074665 | 12/2018 | |
| CN | 110415227 | 11/2019 | |
| CN | 111630525 | 9/2020 | |
| CN | 111757701 | 10/2020 | |
| WO | WO2020163314 A1 * | 2/2020 | ............... G06N 5/01 |

OTHER PUBLICATIONS

International Search Report and Written Opinion for International (PCT) Patent Application No. PCT/US2021/063620, dated Mar. 25, 2022 13 pages.

International Preliminary Report on Patentability for International (PCT) Patent Application No. PCT/US2021/063620, dated Jun. 29, 2023 9 pages.

\* cited by examiner

SYSTEMS AND METHODS FOR MONITORING ONE OR MORE ANATOMICAL ELEMENTS

CROSS REFERENCE TO RELATED APPLICATIONS

This application claims the benefit of U.S. Provisional Application No. 63/128,574, filed on Dec. 21, 2020, and entitled "Systems and Methods for Monitoring One or More Anatomical Elements", which application is incorporated herein by reference in its entirety.

FIELD

The present technology is related generally to monitoring one or more anatomical elements and more particularly, to annotating and updating image(s) to reflect movement of the one or more anatomical elements.

BACKGROUND

An image of a patient, operating room, and/or surgical site may be referenced prior to or throughout a surgical procedure. The image may provide information about anatomical elements or objects that a surgeon or user may reference for guidance. A registration may also be performed based on the image, which may provide relative information between the patient and surgical tools used during the procedure.

SUMMARY

Example aspects of the present disclosure include:

A method for monitoring one or more anatomical elements according to at least one embodiment of the present disclosure comprises receiving an image and a plurality of annotations, the image depicting one or more anatomical elements, the image comprising a plurality of image elements, each annotation corresponding to one of the one or more anatomical elements, each annotation associated with one of the plurality of image elements; receiving movement information about a movement, from a first pose to a second pose, of at least a portion of a particular anatomical element of the one or more anatomical elements; identifying, based on the movement information and the annotations, image elements corresponding to an anatomical region including the particular anatomical element to yield a set of image elements; and adjusting the set of image elements based on the movement information to yield an updated image reflecting changes to affected anatomical elements.

Any of the aspects herein, further comprising: updating a surgical plan based on the updated image.

Any of the aspects herein, wherein the annotations are generating using artificial intelligence.

Any of the aspects herein, wherein each image element of the plurality of image elements is a pixel or a voxel.

Any of the aspects herein, further comprising: comparing the second pose of the particular anatomical element to a target pose of the particular anatomical element.

Any of the aspects herein, wherein each annotation of the plurality of annotations comprises rigidity information about a rigidity of the one of the one or more anatomical elements with which the annotation is associated.

Any of the aspects herein, further comprising: registering the image to a coordinate system, and updating the registration based on the updated image.

Any of the aspects herein, wherein the movement information is sensor data received from at least one sensor, the at least one sensor configured to sense movement of at least the portion of the particular anatomical element.

Any of the aspects herein, wherein at least some of the plurality of annotations comprises information about movement of a tracker disposed on the particular anatomical element.

Any of the aspects herein, wherein the one or more anatomical elements are one or more vertebrae.

Any of the aspects herein, wherein each annotation of the plurality of annotations comprises level information identifying a level of a spinal region of a vertebra of the one or more vertebrae with which the annotation is associated.

A method for monitoring one or more objects according to at least one embodiment of the present disclosure comprises receiving an image comprising a plurality of image elements that collectively depict one or more objects; associating an annotation with each image element to yield one or more annotated image elements, the annotations comprising characteristic information about at least one object of the one or more objects to which the image element corresponds; receiving sensor data about movement of the at least one object to a new pose; identifying, based on the sensor data and the annotations, image elements in the image corresponding to the at least one object to yield a set of image elements; and updating the image by adjusting the set of image elements to depict the at least one object in the new pose.

Any of the aspects herein, wherein the at least one object is at least one of a surgical instrument or an anatomical element.

Any of the aspects herein, wherein the annotation is associated with each image element using artificial intelligence.

Any of the aspects herein, further comprising: registering the image to a coordinate system, and updating the registration based on the updated image.

Any of the aspects herein, further comprising: updating a surgical plan based on the updated image.

Any of the aspects herein, wherein the at least one object is a vertebra and further comprising: comparing the new pose subset of the vertebra to a target pose of the vertebra.

Any of the aspects herein, wherein the at least one object comprises a first object and a second object, wherein the sensor data corresponds to movement of each of the first object and the second object to a new pose, wherein the set of image elements corresponds to the first object and the second object, and wherein the updating the image includes adjusting the set of image elements to depict each of the first object and the second object in the new pose.

Any of the aspects herein, wherein the characteristic information includes information about a relationship between the first object and the second object.

A system for monitoring one or more objects according to at least one embodiment of the present disclosure comprises at least one processor; and at least one memory storing instructions for execution by the at least one processor that, when executed, cause the at least one processor to: receive an image comprising a first plurality of image elements depicting one or more anatomical elements and a second plurality of image elements depicting soft tissue; annotate each image element of the first plurality of image elements as corresponding to one of the one or more anatomical elements and each image element of the second plurality of image elements as corresponding to the soft tissue and as having a movement constraint relative to at least one of the one or more anatomical elements, to yield a plurality of annotations; receive information about a movement, from a first position to a second position, of at least a portion of a particular anatomical element of the one or more anatomical elements; identify, based on the information and the annotations, image elements corresponding to an anatomical region including the portion of the particular anatomical element to yield a set of image elements, the set of image elements include image elements from each of the first plurality of image elements and the second plurality of image elements; and adjust the set of image elements based on the information and the plurality of annotations to yield an updated image showing the particular anatomical element in the second position.

Any of the aspects herein, further comprising: at least one sensor for sensing movement of the one or more objects and wherein the information received is sensor data from the at least one sensor.

Any of the aspects herein, further comprising: a tracker disposed on each of the one or more objects, wherein the information received is information about a movement of the tracker.

Any of the aspects herein, wherein annotating each image element of the plurality of image elements uses artificial intelligence.

Any of the aspects herein, wherein the adjusting comprises interpolating a movement of at least one image element from the second plurality of image elements based on the information.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided herein below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

In a surgical procedure a surgeon may rely upon image(s) of a surgical site to evaluate or plan a surgical procedure or determine if a desired surgical result has been achieved. Further, the image(s) may be used to perform an initial registration process prior to, or as an early step in, a surgical procedure. The images may be two-dimensional (2-D or 2D), three-dimensional (3-D or 3D), or a combination of 2-D and 3-D images. During the surgical procedure, patient anatomy may shift or move. For example, a surgeon may inadvertently or intentionally push or move the patient, the procedure may involve removal of a portion of an anatomical element, or the procedure may involve moving an anatomical element, such as during a spinal procedure. Such movement may require another registration to be performed, which may be time consuming. Further, image(s) taken throughout the procedure are typically static and may not reflect certain relative information of an anatomical element before and after movement of the anatomical element. Thus, there is a need to track and monitor movement of patient anatomy during a surgical procedure, e.g., as identified in image(s).

As described more fully below, methods and systems for monitoring one or more anatomical elements or objects according to at least some embodiments of the present disclosure may beneficially provide an annotated image by which movement of the anatomical elements or objects may be tracked in real-time and, in some embodiments, without the use of ionizing radiation or imaging modalities associated with negative effects from strong radiation exposure. In other words, in some embodiments, X-ray, CT, Fluoroscopy, or the like, are not needed to track anatomical elements or objects in real-time. As a result, in such embodiments, anatomical elements or objects may be tracked in real-time without exposing a patient to X-ray or other ionizing radiation. The annotated image may include image elements that are each annotated to correlate particular image elements to the corresponding anatomical element or object. Thus, when movement of the anatomical element or object is detected, the image element(s) corresponding to the detected anatomical element or object may be computationally adjusted to yield an updated image that shows the detected anatomical element or object in a new position or pose (e.g., position and orientation). More specifically, the image may be computationally updated by a computing device executing software to update the image. The updated image may be a 2D image displayed to a surgeon or other user on a screen, or may be a 3D projection that may be shown to a surgeon or other user using, for example, augmented reality (AR), virtual reality (VR), or mixed reality glasses and/or technology. When using AR/VR/mixed reality, the updated image may be shown as an overlay to the anatomy visible to the surgeon or other user (e.g., as an overlay on a visible portion of the patient's back). Also, the methods and systems described herein may use artificial intelligence or similar processing techniques to annotate or associate each image element to an anatomical element or object.

Embodiments of the present disclosure provide technical solutions to one or more of the problems of (1) tracking and monitoring movement of patient anatomy during a surgical procedure; (2) annotating an image of patient anatomy to identify anatomical elements; (3) updating an image of patient anatomy to show movement of anatomical elements that have moved based on annotations in the image; and (4) providing accurate and updated image(s) of patient anatomy to a user (e.g., a surgeon) during a surgical procedure.

Figure 1:
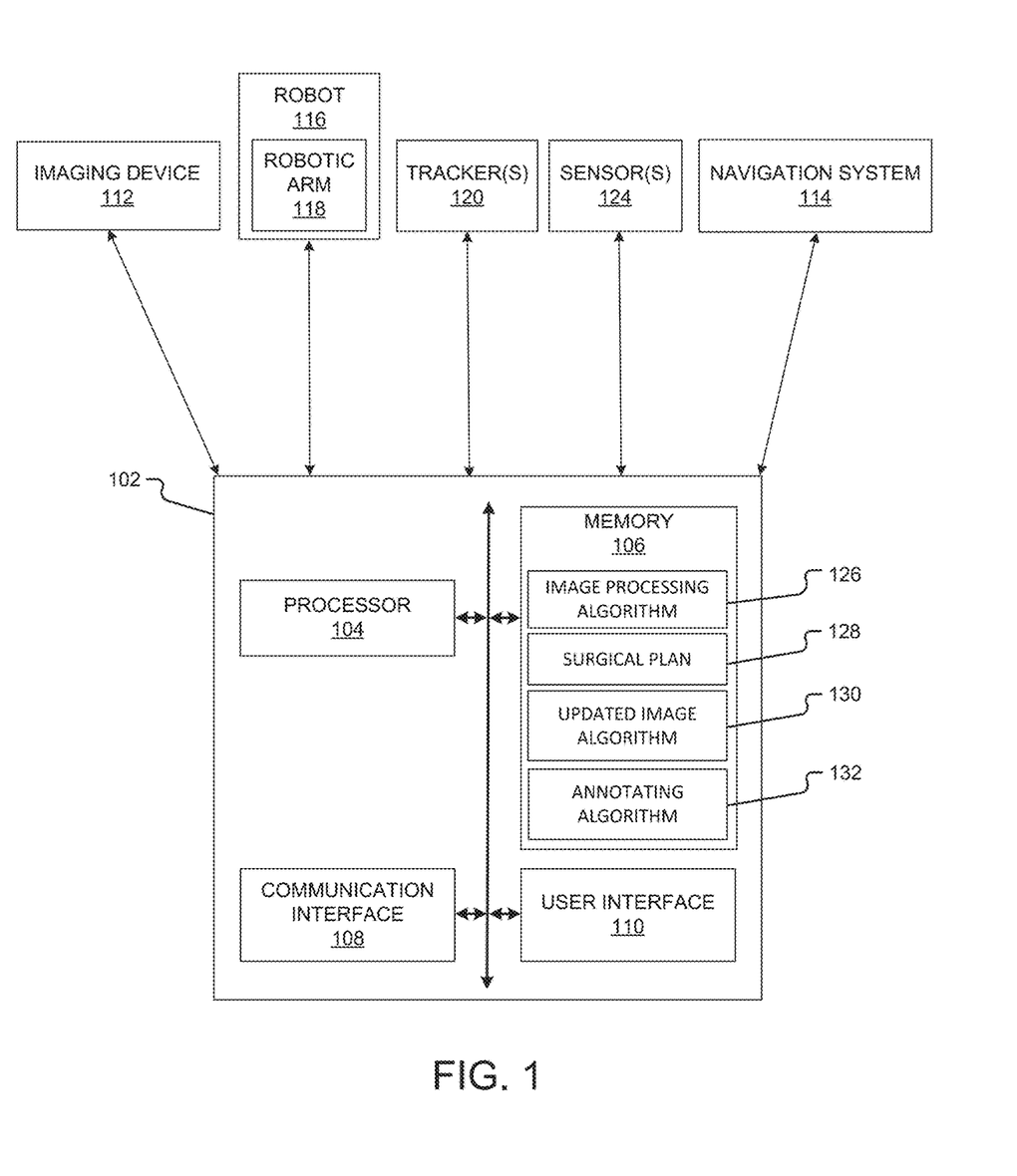
FIG. 1 is a block diagram of a system according to at least one embodiment of the present disclosure.

Turning first to FIG. 1, a block diagram of a system 100 according to at least one embodiment of the present disclosure is shown. The system 100 may be used to process image data; execute an updated image algorithm 130, an annotating algorithm 132, and/or an image processing algorithm 126; and/or carry out other aspects of one or more of the methods disclosed herein. The system 100 comprises a computing device 102, one or more imaging devices 112, a navigation system 114, a robot 116, one or more trackers 120, and/or one or more sensors 124. Systems according to other embodiments of the present disclosure may comprise more or fewer components than the system 100. For example, the system 100 may not include the navigation system 114, the robot 116, the trackers 120, and/or the sensors 124.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 116, the navigation system 114, the tracker 120, and/or the sensor 124.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein. The memory 106 may store, for example, one or more image processing algorithms 126, one or more updated image algorithm 130, one or more annotating algorithms 132, and/or one or more surgical plans 128. Such algorithms may, in some embodiments, be organized into one or more applications, modules, packages, layers, or engines. The algorithms may cause the processor 104 to manipulate data stored in the memory 106 and/or received from the imaging device 112, the robot 116, the navigation system 114, and/or the sensors 124.

The computing device 102 may also comprise a communication interface 108. The communication interface 108 may be used for receiving image data or other information from an external source (such as the imaging device 112, the navigation system 114, the robot 116, and/or the sensor 124), and/or for transmitting instructions, images, or other information to an external system or device (e.g., another computing device 102, the navigation system 114, the imaging device 112, the robot 116, and/or the sensor 124). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding receiving an image depicting one or more anatomical elements, the image comprising a plurality of image elements; to receive a user selection or other user input regarding annotating, using artificial intelligence, each image element of the plurality of image elements as corresponding to one of the one or more anatomical elements to yield a plurality of annotations, each associated with one of the plurality of image elements; to receive a user selection or other user input regarding receiving information about a movement, from a first position or pose to a second position or pose, of at least a portion of a particular anatomical element of the one or more anatomical elements; to receive a user selection or other user input regarding identifying, based on the information and the annotations, each image element corresponding to the particular anatomical element to yield a subset of image elements; to receive a user selection or other user input regarding adjusting the subset of image elements based on the information to yield an updated image showing the particular anatomical element in the second position or pose; to receive a user selection or other user input regarding updating a surgical plan based on the updated image; to receive a user selection or other user input regarding comparing the second position or pose of the particular anatomical element to a target position or pose of the particular anatomical element; to receive a user selection or other user input regarding registering the image to a coordinate system; to receive a user selection or other user input regarding updating the registration based on the updated image; to receive a user selection or other user input regarding receiving an image comprising a plurality of image elements that collectively depict one or more objects; to receive a user selection or other user input regarding associating an annotation with each image element using artificial intelligence to yield one or more annotated image elements, the annotations comprising characteristic information about an object of the one or more objects to which the image element corresponds; to receive a user selection or other user input regarding receiving sensor data about movement of at least one object of the one or more objects to a new pose; to receive a user selection or other user input regarding identifying, based on the sensor data and the annotations, each image element in the image corresponding to the at least one object to yield a subset of image elements; to receive a user selection or other user input regarding updating the image by adjusting the subset of image elements to depict the at least one object in the new pose; and/or to display the images, the updated image, and/or the surgical plan 128. In some embodiments, the user interface 110 may be useful to allow a surgeon or other user to modify the plan 128, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be capable of taking a 2D image or a 3D image to yield an image and/or image data. "Image data" as used herein refers to the data generated or captured by an imaging device, including in a machine-readable form, a graphical form, and in any other form. In various examples, the image data may comprise image elements corresponding to an object or an anatomical feature of the patient or a portion thereof (e.g., a spinal region). Each image element may be a pixel or a voxel and may be annotated as corresponding to an anatomical element as described later in further detail. In some embodiments, each annotation may also include rigidity information about a rigidity of the corresponding anatomical element, information about a tracker disposed on or associated with the corresponding anatomical element, information about a movement of the tracker, and/or in embodiments where the one or more anatomical element is one or more vertebrae, level information identifying a level of a spinal region of a corresponding vertebra.

The imaging device 112 may be or comprise, for example, a camera or a CT scanner, but may also be or comprise a fluoroscope, an ultrasound probe, an O-arm, a C-arm, a G-arm, any other device utilizing X-ray-based imaging, a magnetic resonance imaging (MM) scanner, an optical coherence tomography scanner, an endoscope, a microscope, a thermographic camera (e.g., an infrared camera), or any other imaging device suitable for obtaining images or image data corresponding to an anatomical feature of a patient or an object.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, trackers 120, or other objects within the operating room or other room where a surgery takes place. In some embodiments, the sensor(s) may include an active component that a tracker 120 uses to determine its own position. For example, a tracker 120 may be or comprise an induction coil that works with a transmitter to determine and transmit a pose of the coil in the transmitter's coordinate system. In other embodiments, a tracker may be a passive device detectable by a camera or other sensor.

In various embodiments, the navigation system 114 may be used to track a position or pose of the imaging device 112 (or, more particularly, of a navigated reference marker attached, directly or indirectly, in fixed relation to the imaging device 112) and/or of the robot 116 (or, more particularly, of a navigated reference marker attached, directly or indirectly, in fixed relation to the robot 116). The navigation system 114 may include a display for displaying one or more images from an external source (e.g., the computing device 102, imaging device 112, or other source) or a video stream from the camera or other sensor of the navigation system 114. In some embodiments, the system 100 can operate without the use of navigation system 114.

The robot 116 may be any surgical robot or surgical robotic system. The robot 116 may be or comprise, for example, the Mazor X™ Stealth Edition robotic guidance system. The robot 116 may comprise one or more robotic arms 118. In some embodiments, the robotic arm 118 may comprise a plurality of robotic arms, though the robot 116 may comprise one robotic arm, two robotic arms, or more than two robotic arms. The robotic arm 118 may be used to selectively hold and/or operate one or more imaging devices 112, and/or any other tool or instrument. In some embodiments, the robotic arm 118 has at least five degrees of freedom. In other embodiments, the robotic arm 118 has at least six degrees of freedom. In yet other embodiments, the robotic arm 118 has fewer than five or greater than six degrees of freedom. The robotic arm 118 (and/or a base of the robot 116) may also have three dimensions of orientation. The combination of multiple degrees of freedom and multiple dimensions of orientation allows for the robotic arm 118 to move to any pose. In other words, the robotic arm 118 is not limited to a fixed area and can move in any direction. Further, in some embodiments, the robot 116 can move during a surgical procedure to position or pose the robotic arm 118 (and thus, the imaging device 112).

Reference markers or trackers 120 (e.g., navigation markers) may be placed on the robot 116, the robotic arm 118, the imaging device 112, and/or any other object in the surgical space. The trackers 120 may be tracked by the navigation system 114, and the results of the tracking may be used by the robot 116 and/or by an operator of the system 100 or any component thereof. As described above, in some embodiments, the navigation system 114 can be used to track other components of the system 100 (e.g., the imaging device 112) and the system 100 can operate without the use of the robot 116 (e.g., with the surgeon manually manipulating the imaging device 112).

Sensor(s) 124 may be used to track and/or sense movement of at least one object or anatomical element. The movement may be detected visually, by a change in position or pose of positional data, and/or by a change in a force detected as exerted by the object or anatomical element. In some examples, the sensor 124 may trigger the computing device 102 to determine a position or pose of an object or an anatomical element based on the sensor data and compare the determined position or pose with an expected position or pose of the object or the anatomical element to determine if the object or the anatomical element has moved.

The sensor 124 may be any kind of sensor 124. The sensor 124 may be configured for measuring the movement of the anatomical element or the object. The sensor 124 may include one or more or any combination of components that are electrical, mechanical, electro-mechanical, magnetic, electromagnetic, or the like. The sensor 124 may include, but is not limited to, one or more of a camera, a torque sensor, a force sensor, a linear encoder, a rotary encoder, a capacitor, magnetometers, induction coils, and/or an accelerometer. In some embodiments, the sensor 124 may include a memory for storing sensor data. In still other examples, the sensor 124 may output signals (e.g., sensor data) to one or more sources (e.g., the computing device 102, the navigation system 114, and/or the robot 116).

The sensor 124 may be positioned adjacent to or integrated with another component of the system 100 such as, but not limited to, the robotic arm 118, the imaging device 112, the tracker 120, the computing device 102, and/or the navigation system 114. In some embodiments, the sensor 124 is positioned as a standalone component. The sensor 124 may include a plurality of sensors and each sensor may be positioned at the same location or a different location as any other sensor. It will be appreciated that in some embodiments the sensor(s) 124 can be positioned at or on any component of the system 100 or environment (e.g., on any portion of the navigation system 114, the robot 116, the robotic arm 118, and/or any other component at the surgical site).

The sensor 124 may send the data to the computing device 102 when the sensor 124 detects movement of the object or the anatomical element or may continuously send data to the computing device 102. Further, in some embodiments, the sensor 124 may send data to the computing device 102 to display on the user interface 110 or otherwise notify the surgeon or operator of the movement. In other embodiments, the sensor 124 may alert the surgeon or operator of the movement by an alert such as, but not limited to, a sound or a light display. The sensor 124 may advantageously provide a safety function by monitoring and alerting the surgeon or operator of the movement interfering with the procedure.

Figure 2:
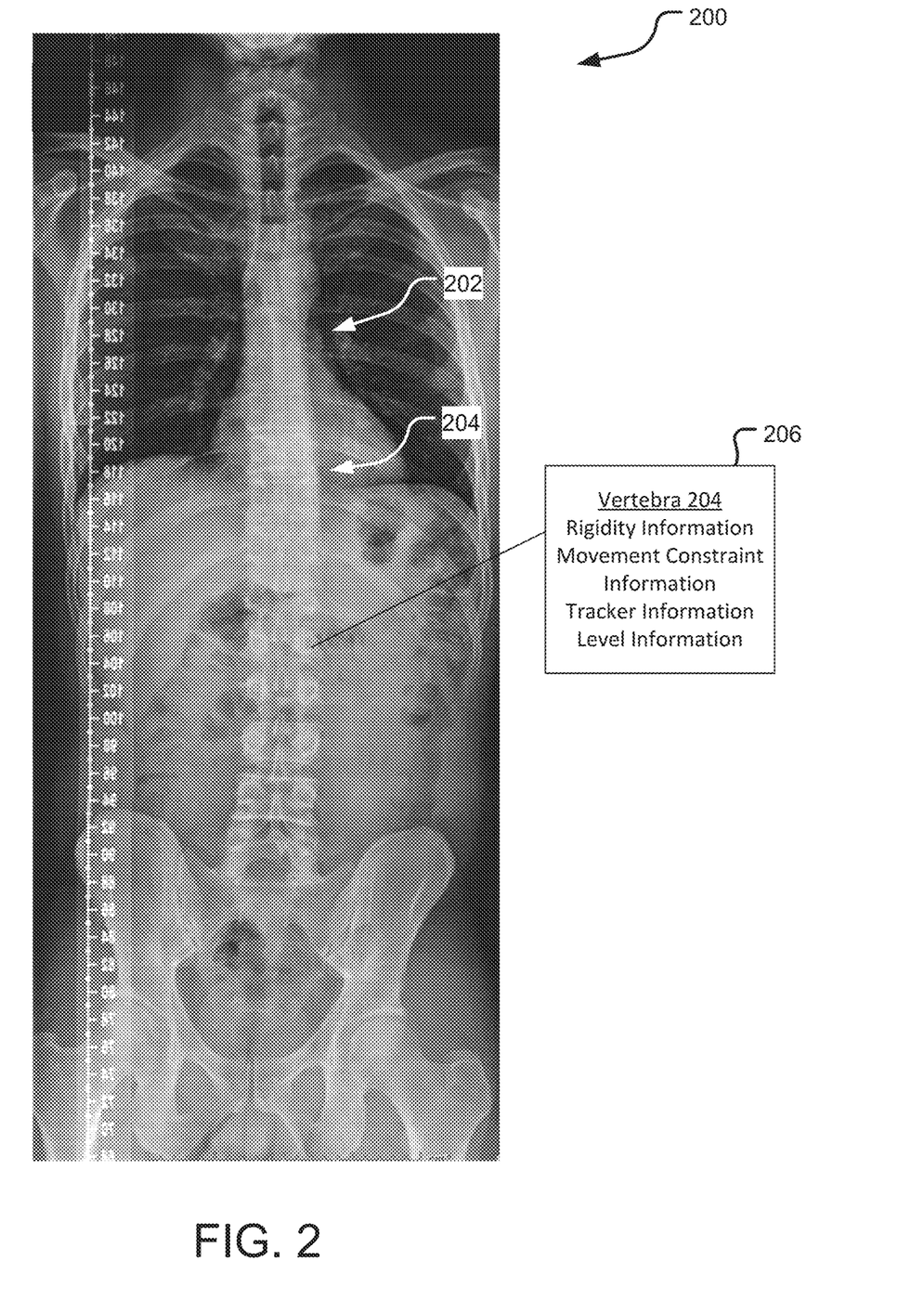
FIG. 2 is an example X-ray image depicting one or more anatomical elements.

Turning to FIG. 2, an X-ray image 200 depicting a spinal region 202 and a plurality of vertebrae 204 is shown. A form of annotation 206 is shown for illustrative purposes. In some embodiments, the annotation may be in machine-readable form. In other embodiments, the annotation may be in a graphical form, or in any other form. As illustrated, the annotation 206 for an image element provides information to correspond or correlate the image element to a specific vertebra 204. The annotation 206 may also provide information about a rigidity of the vertebra 204. The rigidity information may include a Young's modulus of the anatomical element or object, which may be used to determine if a portion or an entirety of the anatomical element or object moves and if so by how much. For example, a less rigid anatomical element or object may move a distance that is less than a more rigid anatomical element or object. The annotation 206 may also provide information about a tracker such as the tracker 120 corresponding to the vertebra 204. The tracker information may include information about a tracker 120 associated with the vertebra 204 and/or may include information about movement of the tracker 120 (and thus movement of the vertebra 204). The annotation 206 may also include level information identifying a level of the spinal region 202 of the vertebra 204, which may aid in identifying and/or classifying the vertebra 204.

The annotation 206 may also comprise information about any movement constraints of the object or anatomical element relative to another object or anatomical element. For example, if two vertebrae are fused together, then the annotations for the image elements associated with the two vertebrae may indicate such fusion. In the same example, if movement of one of the two vertebrae is detected, then the system can update a position or pose of the image elements for both of the fused vertebrae accordingly. In another example, the annotation may include information about two vertebrae connected by a disc. In the same example, if movement of a first vertebra of the two vertebrae is detected, then the system can update a position or pose of the image elements for both of the two vertebrae accordingly. Further, movement of a second vertebra can be adjusted based on a property of the disc (i.e., flexibility) as reflected and/or stored in the annotation.

The annotation 206 may also comprise information about soft tissue surrounding, connected to, or otherwise associated with other objects and/or anatomical element. (The one or more anatomical elements may, in some embodiments, include soft tissue. In other embodiments, however, whether due to limitations of a given imaging modality or for any other reason, the one or more anatomical elements may comprise only hard tissue elements. Regardless of whether the soft tissue of an anatomical region depicted in an image is explicitly identified as an anatomical element or not, the soft tissue may be annotated as described herein.) The information may include movement constraints of the soft tissue. For example, if a vertebra moves, soft tissue surrounding or adjacent the vertebra—such as, for example, an intervertebral disc, ligament, muscle, or nerve—may necessarily move or shift in a particular way to accommodate movement of the vertebra. Using movement constraints contained within the annotation, then, a movement of soft tissue, even if not directly measurable or detectable, may in some embodiments be determined by interpolation based on information about observed or otherwise detected movement of other anatomical elements.

Annotations such as the annotation 206 may be provided for every pixel and/or voxel of an image that corresponds to an anatomical element. In some embodiments, pixels and/or voxels corresponding to a single anatomical element are linked in any known way, and a single annotation 206 is provided for that anatomical element. In some embodiments, each anatomical element in the image may be annotated, while in other embodiments, a subset of the anatomical elements in the image may be annotated. The annotations may be provided for hard tissue anatomical elements as well as for soft tissue anatomical elements.

Figure 3:
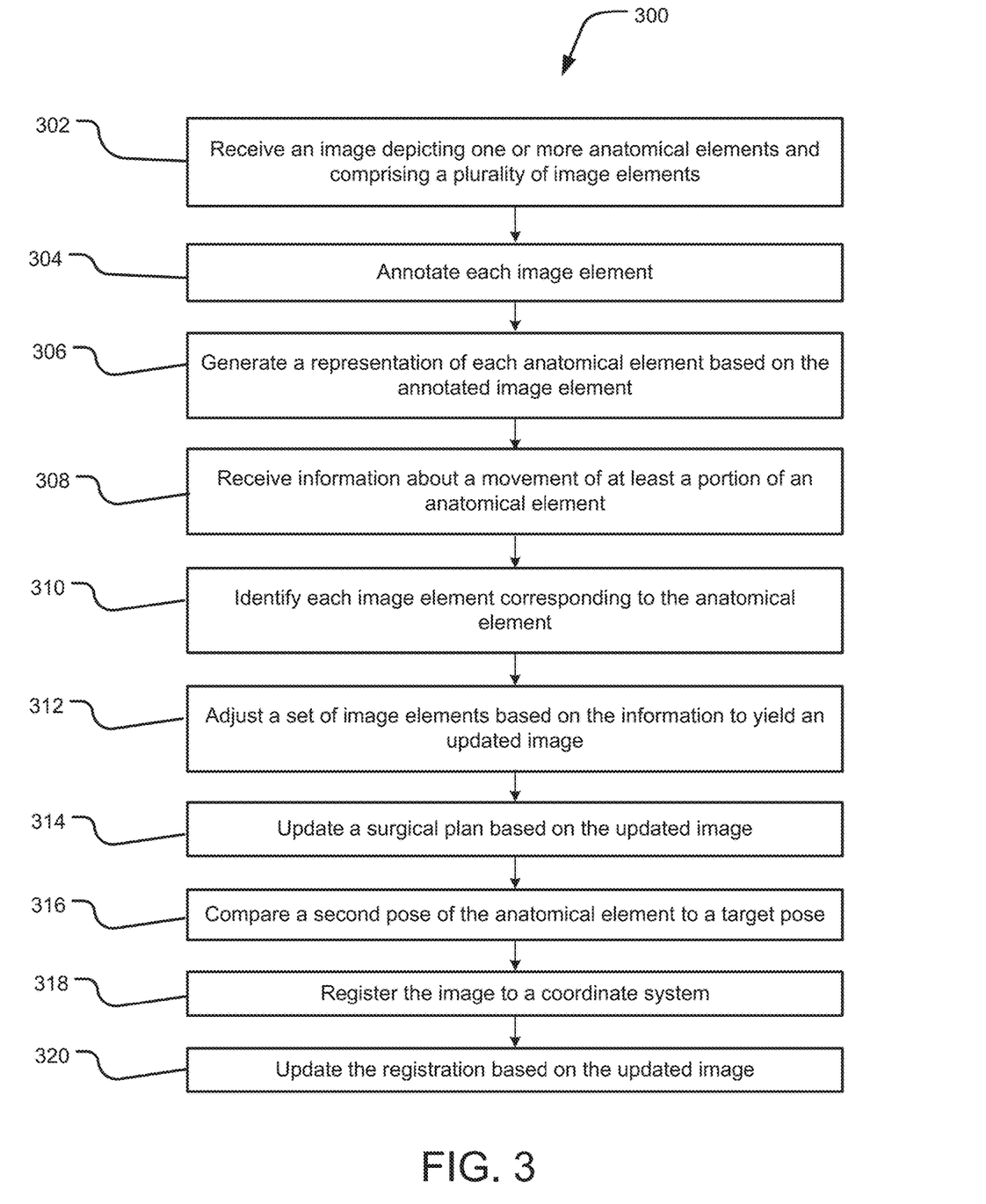
FIG. 3 is a flowchart of a method according to at least one embodiment of the present disclosure.

Turning now to FIG. 3, a method 300 for monitoring one or more anatomical elements may be carried out or otherwise performed, for example, by at least one processor. The at least one processor may be the same as or similar to the processor(s) 104 of the computing device 102 described above. The at least one processor may be part of a robot (such as a robot 116) or part of a navigation system (such as a navigation system 114). A processor other than any processor described herein may also be used to execute the method 300. The at least one processor may perform the method 300 by executing instructions stored in a memory (such as the memory 106). The instructions may correspond to one or more steps of the method 300 described below. One or more aspects of the method 300 may be performed by or with a surgical robot and/or a surgeon.

The method 300 comprises receiving an image depicting one or more anatomical elements (step 302). The image comprises a plurality of image elements. Each image element is a pixel (for 2D images) or a voxel (for 3D images) and may be annotated, as described with respect to step 304. The one or more anatomical elements may be one or more vertebrae. The image may depict at least a portion of an anatomical element. In some embodiments, the image may also depict at least a portion of a tracker such as the tracker 120. The tracker may be used by a navigation system such as the navigation system 114 to determine a pose (e.g., a position and an orientation) or a position of the corresponding anatomical element.

The image may be received or obtained from an imaging device such as the imaging device 112, which may be any imaging device such as a camera, X-ray based imaging device, or ultrasound imaging device. The image may comprise one or more 2D images, one or more 3D images, or a combination of one or more 2D images and one or more 3D images. In some embodiments, one imaging device may be used to obtain the image. In other embodiments, multiple imaging devices may be used to obtain the image. In examples wherein more than one image is received or multiple images are used to construct a 3D image, a first imaging device may obtain a first one of the images independently of a second imaging device obtaining a second one of the images. In another example, at least a first one of the images may be obtained with a first imaging device and at least a second one of the images may be obtained with a second imaging device. In other embodiments, the image may be received via a user interface such as the user interface 110 and/or via a communication interface such as the communication interface 108 of a computing device such as the computing device 102, and may be stored in a memory such as the memory 106. The image may also be generated by and/or uploaded to any other component of the system 100. In some embodiments, the image may be indirectly received via any other component of the system 100 or a node of a network to which the system 100 is connected.

The image may be processed using an image processing algorithm such as the image processing algorithm 126 to identify the anatomical element(s) in the image. In some embodiments, feature recognition may be used to identify a feature of the anatomical element. For example, a contour of a vertebra, femur, or other bone may be identified in the image. In other embodiments, the image processing algorithm may be based on artificial intelligence or machine learning. In such embodiments, a plurality of training images may be provided to a processor such as the processor 104, and each training image may be annotated to include identifying information about an anatomical element in the image. The processor, executing instructions stored in memory such as the memory 106 or in another memory, may analyze the images using a machine-learning algorithm and, based on the analysis, generate one or more image processing algorithms such as the image processing algorithms 126 for identifying anatomical elements in an image. Such image processing algorithms 126 may then be applied to the image received in step 302, as described above.

The method 300 also comprises annotating each image element of the plurality of image elements as corresponding to one of the one or more anatomical elements or to soft tissue to yield a plurality of annotations (step 304). The annotating may use artificial intelligence to annotate each image element. The annotating may be based on the anatomical element(s) identified in the image processing described with respect to step 302. The annotating may use an annotating algorithm such as the annotating algorithm 132 to annotate each image element. In some embodiments, the artificial intelligence may be a convolutional neural network. Though in other embodiments, the artificial intelligence may be, but is not limited to, machine learning or any type of neural network (e.g., feedforward neural network, radial basis function neural network, Kohonen neural network, recurrent neural network, modular neural network, adversarial networks, autoencoders, or the like).

Each annotation is associated with one of the plurality of image elements. Each annotation may comprise rigidity information about a rigidity of the anatomical element or soft tissue with which the annotation is associated. In embodiments where the one or more anatomical elements are one or more vertebrae, each annotation may also comprise level information identifying a level of a spinal region of a vertebra of the one or more vertebrae with which the annotation is associated. In some embodiments, one or more of the plurality of annotations may comprise information about movement of a tracker such as the tracker 120 disposed on the particular anatomical element. Further, in some embodiments (particularly embodiments in which a user interface such as the user interface 110 is utilized to display information for a surgeon or other user), each annotation may include a color or may change a color of the associated image element. Thus, for example, a first group of image elements associated with a first vertebra may be a first color and a second group of image elements associated with a second vertebra may be a second color.

It will be appreciated that in some embodiments, the step 304 is omitted, as the annotations may be received with the image in step 302.

The method further comprises generating a representation of each anatomical element based on the annotated image elements (step 306). In examples where the annotated image elements are voxels, a mesh may be generated to represent the one or more anatomical elements based on the annotated image elements. In other words, a mesh may be formed for each anatomical element. For example, a first mesh may be formed for a first anatomical element and a second mesh may be formed for a second anatomical element. In other embodiments, any visual representation may be generated or derived from the annotated image elements.

The method 300 further comprises receiving information about a movement, from a first position or pose to a second position or pose, of at least a portion of a particular anatomical element of the one or more anatomical elements (step 308). In some embodiments, the information is sensor data received from at least one sensor, such as the sensor 124. The sensor may be configured to track and/or sense movement of the particular anatomical element (and/or of a tracker 120 attached to the particular anatomical element). The movement may be detected visually (e.g., by a camera), by a change in position or pose of positional data, and/or by a change in a force detected as exerted by the particular anatomical element. In some examples, the sensor may trigger a computing device such as the computing device 102 to determine a position or pose of an anatomical element based on the sensor data and compare the determined position or pose with an expected position or pose of the anatomical element to determine if the anatomical element has moved. In other examples, an accelerometer may be disposed on the particular anatomical element and a change in an acceleration force as detected by the accelerometer may indicate that the particular anatomical element has moved. In other embodiments, the information is navigation data received from a navigation system such as the navigation system 114. The navigation data may include information about movement of a tracker such as the tracker 120, which may be attached to or otherwise associated with the particular anatomical element.

The method 300 also comprises identifying, based on the information and the annotations, each image element corresponding to the particular anatomical element to yield a set of image elements (step 310). In other words, each image element annotated as associated with the particular anatomical element is identified as part of the set of image elements and the set of image elements corresponds to the particular anatomical element depicted in the image. The set of image elements may also include image elements corresponding to soft tissue affected by movement of the particular anatomical element. The identifying may be based on the information described in step 304 such as, but not limited to, rigidity information, tracker information, movement constraint information, and/or level information.

The method also comprises adjusting the set of image elements based on the information to yield an updated image showing the particular anatomical element in the second position or pose (step 312). The updated image may be generated using an updated image algorithm such as the updated image algorithm 130 to show the particular anatomical element in the second position or pose. The updated image may also show soft tissue affected by movement of the particular anatomical element in a new pose. In other words, image elements corresponding to soft tissue may also be adjusted in the step 312, whether based on detected motion thereof, application of one or more motion constraints identified in one or more annotations corresponding to such image elements, interpolation, a combination of any of the foregoing, or otherwise.

In some embodiments, adjusting the set of image elements may include identifying the second position or pose in the image (which may occur as part of the step 308 or the step 312) and defining a second set of image elements (which may correspond, for example, to a tracker, or to a portion of an anatomical element) comprising the image elements at the second position or pose. A first set of image elements includes the set of image elements showing the particular anatomical element. The adjusting may include changing the first set of image elements to properly align with the entirety of the first set of image elements, thereby depicting the particular anatomical element in the second position or pose. In other words, if received information indicates that a tracker affixed to a vertebra (which is known to be rigid) has moved, then the step 312 comprises adjusting every pixel or voxel corresponding to the vertebra to restore a relative position or pose of each such pixel or voxel to the tracker. The adjusting may also include determining whether the second set of image elements has moved to a third position or pose or has been removed.

The updated image may distinguish between image elements whose position is known (e.g., image elements corresponding to the anatomical element(s) determined to have moved in the step 308) from image elements whose position is estimated (e.g., based on movement constraints and/or interpolation). In other words, the updated image may show not only an updated position of a particular anatomical element (which updated position is based on information about a movement of the particular anatomical element), but also an updated position or pose of other anatomical elements and/or soft tissue in the image (which updated position is based on estimates, interpolation, or other indirect determination methods). In such embodiments, the image elements whose updated position is estimated may have a lower intensity than the image elements whose updated position is known, or may be otherwise visually distinguishable from the image elements whose updated position is known, so as to convey to a surgeon or other user that the positions of such image elements have been estimated and may be incorrect or otherwise inaccurate.

The method 300 also comprises updating a surgical plan such as the surgical plan 128 based on the updated image (step 314). The surgical plan may be received via a user interface (e.g., the user interface 110) and/or a communication interface (e.g., the communication interface 108) of a computing device such as the computing device 102, and may be stored in a memory such as the memory 106 of the computing device 102. The surgical plan includes information about the anatomical element. The information may include information about a target position or pose and/or orientation of the anatomical element. The information may also include at least one dimension of the anatomical element, which may be useful in determining movement of the anatomical element. The information may also include information about placement of an instrument or implant (e.g., a pedicle screw). The surgical plan may be updated to adjust the information and/or to adjust at least one surgical step based on the updated image. For example, a tool path may be adjusted to avoid an object that has moved into a current path of the tool.

The method 300 also comprises comparing the second position or pose of the particular anatomical element to the target position or pose of the particular anatomical element (step 316). The target position or pose may be obtained from a surgical plan such as the surgical plan 128. The comparison may include measuring a difference in position, angle, orientation, dimension, or the like between the second position or pose and the target position or pose. In some embodiments, a surgical procedure may result in movement of an anatomical element. For example, in a spinal fusion procedure, a rod and pedicle screws may be installed to aid in realignment of the patient's spine during fusion. During the procedure, one or more vertebrae may move to conform to a shape of the rod when the rod in installed and secured in each pedicle screw. Thus, comparing a vertebra at a determined second position or pose to a target position or pose as defined by the procedure may guide or inform a surgeon or user of the accuracy of the movement and/or of the success of the surgical procedure (or an aspect thereof).

For example, if a difference in the second position or pose and the target position or pose exceeds a threshold, then the surgeon may need to repeat a step of the procedure to reduce the difference between the second position or pose and the target position or pose. Conversely, the comparison may inform the surgeon that the step (or procedure) was performed correctly.

The method 300 also comprises registering the image to a coordinate system (step 318). The registration may correlate the image to a patient in a common coordinate system. In some embodiments, the registration may utilize current images of the patient to correlate the image to the patient. In the same embodiments, the image may be mapped to the current image space and from the current image space to the patient space, and enable a determination of the relative positions and/or orientations of the patient's anatomical features between a first orientation of the patient (e.g., when the earlier or initial image was taken) and a second orientation of the patient (e.g., when the current image was taken). Registering the image space to the patient space may occur with or without a fiducial marker. In other embodiments, the method 300 may register the image to a navigation coordinate system used by a navigation system such as the navigation system 114.

The method 300 also comprises updating the registration based on the updated image (step 320). The updating may include determining an updated pose or position of the anatomical element based on the information received in step 306 and updating the registration based on the updated pose or position. The updated image may be displayed on a user interface such as the user interface 110 for viewing by a surgeon or user. In some embodiments, the user interface is a monitor. In other embodiments, the user interface is a headset or eyewear worn by the surgeon. The headset or eyewear may incorporate virtual reality, augmented reality or mixed reality and may show a 2D image or 3D model of the anatomical element in virtual reality or overlaid over an actual anatomical element visible through the headset or eyewear. In such embodiments, updating the image may update the 2D image or 3D model displayed in the headset or eyewear in real-time.

It will be appreciated that the steps 302-320 may be repeated throughout a surgical procedure so as to provide updated information about movement of an anatomical element. Further, the updated information may be useful for updating a registration, thereby reducing or eliminating the time associated with a full re-registration process.

Figure 4:
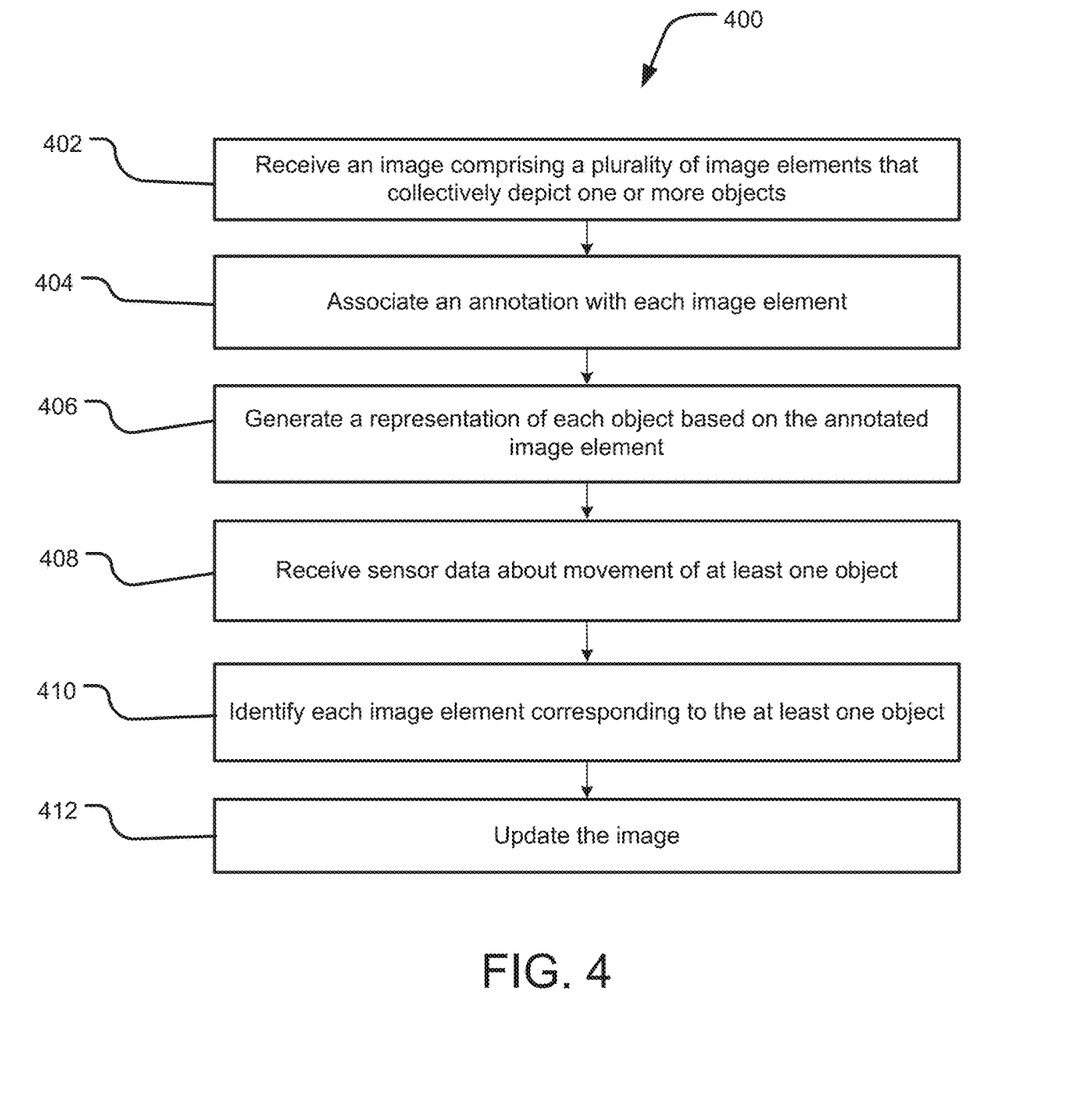
FIG. 4 is a flowchart of a method according to at least one embodiment of the present disclosure.

Turning now to FIG. 4, a method 400 for monitoring one or more anatomical elements may be carried out or otherwise performed, for example, by at least one processor. The at least one processor may be the same as or similar to the processor(s) 104 of the computing device 102 described above. The at least one processor may be part of a robot (such as a robot 116) or part of a navigation system (such as a navigation system 114). A processor other than any processor described herein may also be used to execute the method 400. The at least one processor may perform the method 400 by executing instructions stored in a memory (such as the memory 106). The instructions may correspond to one or more steps of the method 400 described below. One or more aspects of the method 400 may be performed by or with a surgical robot and/or a surgeon.

The method 400 comprises receiving an image comprising a plurality of image elements that collectively depict one or more objects (step 402). In some embodiments, the step 402 is the same as the step 302 of the method 300 described above. In other embodiments, the step 402 is similar to the step 302 of the method 300 described above. For example, the plurality of image elements may depict one or more objects or a combination of one or more objects and/or one or more anatomical elements. The one or more objects may be, but are not limited to, a surgical instrument, a surgical tool, a pedicle screw, and/or a rod.

The method 400 also comprises associating an annotation with each image element to yield one or more annotated image elements (step 404). The associating may use artificial intelligence to associate the annotation with each image element. In some embodiments, the step 404 is the same as the step 304 of the method 300 described above. In other embodiments, the step 404 is similar to the step 304 of the method 300 described above. For example, the annotations may include characteristic information about an object of the one or more objects to which the image element corresponds to. The characteristic information about the object may include, but is not limited to, dimensions of the object, a material of the object, or a type of the object. The characteristic information may also include information about a relationship between a first object and a second object. The annotations may be made automatically, using a convolutional neural network or other neural network. In some embodiments, the annotations may be made using any other form of machine learning or artificial intelligence.

It will be appreciated that in some embodiments, the step 404 is omitted, as the annotations may be received with the image in step 402.

The method further comprises generating a representation of each object based on the annotated image elements (step 406). In some embodiments, the step 406 is the same as the step 306 of the method 300 described above. In other embodiments, the step 406 is similar to the step 306 of the method 300 described above.

The method 400 also comprises receiving sensor data about movement of at least one object of the one or more objects to a new pose (step 408). In some embodiments, the step 408 is the same as the step 308 of the method 300 described above. In other embodiments, the step 408 is similar to the step 308 of the method 300 described above. The sensor data may correspond to detected movement of a tracker or sensor attached to an anatomical element, or to detected movement of a portion of the anatomical element.

The method 400 also comprises identifying, based on the sensor data and/or the annotations, each image element in the image corresponding to the at least one object to yield a subset of image elements (step 410). In some embodiments, the step 410 is the same as the step 310 of the method 300 described above. In other embodiments, the step 410 is similar to the step 310 of the method 300 described above. The identifying may comprise utilizing the annotations to identify an entirety of the image elements that correspond to the tracker, sensor, or anatomical element portion of which movement was detected. In other words, the identifying may comprise utilizing the annotations to identify every image element that depicts a portion of the anatomical element to which the tracker or sensor is affixed, or that includes the portion of the anatomical element that was determined to have moved in the step 408 above.

The method 400 also comprises updating the image by adjusting the subset of image elements to depict the at least one object in the new pose (step 412). In some embodiments, the step 412 is the same as the step 312 of the method 300 described above. In other embodiments, the step 412 is similar to the step 312 of the method 300 described above. In some embodiments, the step 412 also comprises updating a position or pose of one or more other anatomical elements depicted in the image based on a known relationship between movement of the object and movement of the one or more other anatomical elements. Thus, for example, where the at least one object includes a two pedicle screws connected by a rod and the one or more anatomical elements includes two vertebrae in which the pedicle screws are implanted, then the image elements corresponding to the two vertebrae may be adjusted to depict the two vertebrae in their proper relationship to the pedicle screws and rod. In further embodiments where the at least one object is a first object and a second object, the step 412 comprises updating a position or pose of a first object and a second object.

Methods and systems for tracking and monitoring one or more anatomical elements or one or more objects according to at least some embodiments of the present disclosure beneficially annotate individual image elements in an image to identify subsets of image elements that are associated with an anatomical element or object. The annotation combined with information about movement of the anatomical elements or objects may be used to accurately update the associated subset of image elements in the image. Thus, the image may be updated to show the change in the anatomical element or object in the image and may provide beneficial information to a surgeon or user. For example, the surgeon may determine if the movement resulted in movement of the anatomical element or object to a target position or pose. Further, the information and updated image may be used to locally update a registration and avoid a need to perform a full re-registration process.

As may be appreciated based on the foregoing disclosure, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the method 300 and 400). One or more steps of the methods described herein may be performed in an order other than the order in which they are described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for monitoring one or more anatomical elements comprising:
    receiving an image and a plurality of annotations, the image depicting one or more anatomical elements, the image comprising a plurality of image elements, each annotation corresponding to one of the one or more anatomical elements, each annotation associated with one of the plurality of image elements;
    receiving movement information about a movement, from a first pose to a second pose, of at least a portion of a particular anatomical element of the one or more anatomical elements;
    identifying, based on the movement information and the annotations, image elements corresponding to an anatomical region including the particular anatomical element to yield a set of image elements; and
    adjusting the set of image elements based on the movement information to yield an updated image reflecting changes to affected anatomical elements,
        wherein each annotation of the plurality of annotations comprises rigidity information about a rigidity of the one of the one or more anatomical elements with which the annotation is associated.

2. The method of claim 1, further comprising:
    updating a surgical plan based on the updated image.

3. The method of claim 1, wherein each image element of the plurality of image elements is a pixel or a voxel.

4. The method of claim 1, further comprising:
    comparing the second pose of the particular anatomical element to a target pose of the particular anatomical element.

5. The method of claim 1, further comprising:
    registering the image to a coordinate system, and updating the registration based on the updated image.

6. The method of claim 1, wherein the movement information is sensor data received from at least one sensor, the at least one sensor being configured to sense movement of at least the portion of the particular anatomical element.

7. The method of claim 1, wherein at least some of the plurality of annotations comprise information about movement of a tracker disposed on the particular anatomical element.

8. The method of claim 7, wherein each annotation of the plurality of annotations comprises level information identifying a level of a spinal region of a vertebra with which the annotation is associated.

9. A system for monitoring one or more objects comprising:
    at least one processor; and
    at least one memory storing instructions for execution by the at least one processor that, when executed, cause the at least one processor to:
        receive an image comprising a first plurality of image elements depicting one or more anatomical elements and a second plurality of image elements depicting soft tissue;
        annotate each image element of the first plurality of image elements as corresponding to one of the one or more anatomical elements and each image element of the second plurality of image elements as corresponding to the soft tissue and as having a movement constraint relative to at least one of the one or more anatomical elements, to yield a plurality of annotations;
        receive information about a movement, from a first position to a second position, of at least a portion of a particular anatomical element of the one or more anatomical elements;
        identify, based on the information and the plurality of annotations, image elements corresponding to an anatomical region including the portion of the particular anatomical element to yield a set of image elements, the set of image elements including image elements from each of the first plurality of image elements and the second plurality of image elements; and
        adjust the set of image elements based on the information and the plurality of annotations to yield an updated image showing the particular anatomical element in the second position.

10. The system of claim 9, further comprising:
    at least one sensor for sensing movement of the one or more anatomical elements, wherein the information received is sensor data from the at least one sensor.

11. The system of claim 9, further comprising:
    a tracker disposed on each of the one or more anatomical elements,
    wherein the information received is information about a movement of the tracker.

12. The system of claim 9, wherein the adjusting comprises interpolating a movement of at least one image element from the second plurality of image elements based on the information.

* * * * *